US010626242B2

(12) United States Patent
Ferreira et al.

(10) Patent No.: US 10,626,242 B2
(45) Date of Patent: Apr. 21, 2020

(54) PLASTIC COMPOUND AND PREPARATION PROCESS

(71) Applicants: CARBIOS, Saint-Beauzire (FR); CENTRE NATIONAL DE LA RECHERCHE SCIENTIFIQUE, Paris (FR); UNIVERSITE DE POITIERS, Poitiers (FR)

(72) Inventors: Thierry Ferreira, Iteuil (FR); Frederique Guillamot, Gerzat (FR); Steven Colas, Reims (FR)

(73) Assignees: CARBIOS, Saint-Beauzire (FR); CENTRE NATIONAL DE LA RECHERCHE SCIENTIFIQUE, Paris (FR); UNIVERSITE DE POITIERS, Poitiers (FR)

( * ) Notice: Subject to any disclaimer, the term of this patent is extended or adjusted under 35 U.S.C. 154(b) by 0 days.

(21) Appl. No.: 15/536,765

(22) PCT Filed: Dec. 18, 2015

(86) PCT No.: PCT/EP2015/080557
§ 371 (c)(1),
(2) Date: Jun. 16, 2017

(87) PCT Pub. No.: WO2016/097325
PCT Pub. Date: Jun. 23, 2016

(65) Prior Publication Data
US 2017/0349723 A1 Dec. 7, 2017

(30) Foreign Application Priority Data
Dec. 19, 2014 (EP) ..................... 14307116

(51) Int. Cl.
*C08J 11/10* (2006.01)
*C12N 9/02* (2006.01)
*C12N 9/08* (2006.01)
*C12N 9/04* (2006.01)

(52) U.S. Cl.
CPC ........... *C08J 11/105* (2013.01); *C12N 9/0006* (2013.01); *C12N 9/0008* (2013.01); *C12N 9/0061* (2013.01); *C12N 9/0065* (2013.01); *C12N 9/0067* (2013.01); *C12N 9/0069* (2013.01); *C12N 9/0071* (2013.01); *C12N 9/0073* (2013.01); *C12N 9/0077* (2013.01); *C12Y 110/03002* (2013.01); *C08J 2323/02* (2013.01); *C08J 2323/06* (2013.01); *Y02W 30/702* (2015.05)

(58) Field of Classification Search
None
See application file for complete search history.

(56) References Cited

U.S. PATENT DOCUMENTS

| 5,032,512 A * | 7/1991 | Witholt .................. C12N 15/00 435/123 |
|---|---|---|
| 5,145,779 A | 9/1992 | Pometto et al. |
| 5,212,219 A | 5/1993 | Griffin |
| 5,316,847 A | 5/1994 | Suominen |
| 5,378,738 A | 1/1995 | Deguchi et al. |
| 5,426,047 A | 6/1995 | Ito et al. |
| 6,312,578 B1 | 11/2001 | Canivenc et al. |
| 6,429,006 B1 | 8/2002 | Porro et al. |
| 7,465,575 B2 | 12/2008 | Nilsson |
| 7,534,597 B2 | 5/2009 | Hause et al. |
| 7,960,154 B1 | 6/2011 | Nakajima et al. |
| 8,137,953 B2 | 3/2012 | Miller et al. |
| 8,476,056 B2 | 7/2013 | Hoang et al. |
| 8,614,076 B2 | 12/2013 | Wada et al. |
| 8,859,260 B2 | 10/2014 | Sawai et al. |
| 9,476,073 B2 | 10/2016 | Boisart |
| 9,528,132 B2 | 12/2016 | Mazzoli et al. |
| 10,124,512 B2 | 11/2018 | Boisart et al. |
| 2005/0261465 A1 | 11/2005 | Nagarajan |
| 2006/0106120 A1 | 5/2006 | Abe et al. |
| 2011/0008855 A1 | 1/2011 | Park et al. |
| 2011/0200771 A1 | 8/2011 | Barclay |
| 2011/0245057 A1 * | 10/2011 | Scoledes ............... B65F 1/0006 493/227 |
| 2011/0319588 A1 | 12/2011 | Coupin et al. |
| 2012/0184005 A1 | 7/2012 | Ferreira et al. |
| 2013/0274373 A1 | 10/2013 | Yoshikawa et al. |
| 2014/0303278 A1 | 10/2014 | Ferreira et al. |
| 2015/0056673 A1 | 2/2015 | Boisart |
| 2015/0290840 A1 | 10/2015 | Boisart et al. |
| 2016/0280881 A1 | 9/2016 | Boisart et al. |
| 2017/0114205 A1 | 4/2017 | Maille |
| 2017/0313998 A1 | 11/2017 | Alvarez et al. |
| 2018/0051264 A1 | 2/2018 | Li et al. |
| 2018/0142097 A1 | 5/2018 | Guemard et al. |
| 2018/0186943 A1 | 7/2018 | Chateau et al. |

FOREIGN PATENT DOCUMENTS

| CN | 101 457 218 | 6/2009 |
| CN | 102675712 | 9/2012 |
| CN | 103980535 | 8/2014 |
| EP | 0 421 413 | 4/1991 |
| EP | 0 738 752 | 10/1996 |

(Continued)

OTHER PUBLICATIONS

Albertsson, A-C. et al. "Chemistry and biochemistry of polymer biodegradation" *Chemistry and Technology of Biodegradable Polymers*, Jan. 1, 1994, pp. 7-17, Section 2.

(Continued)

*Primary Examiner* — Robert T Butcher
(74) *Attorney, Agent, or Firm* — Saliwanchik, Lloyd & Eisenschenk

(57) ABSTRACT

The invention relates to a plastic compound comprising at least one polyolefin and a biological entity that degrades said polyolefin. The invention further relates to a process for preparing a plastic article wherein at least one polyolefin and one biological entity that degrades said polyolefin are mixed at a temperature at which the polyolefin is in a partially or totally molten state.

19 Claims, No Drawings

(56) References Cited

FOREIGN PATENT DOCUMENTS

| | | |
|---|---|---|
| EP | 1 548 053 | 6/2005 |
| EP | 2 013 280 | 1/2009 |
| EP | 2 348 122 | 7/2011 |
| EP | 2 377 945 | 10/2011 |
| EP | 2 471 910 | 7/2012 |
| EP | 2 626 386 | 8/2013 |
| JP | 2000-506442 | 5/2000 |
| JP | 2002-293982 | 10/2002 |
| JP | 2002-320499 | 11/2002 |
| JP | 2002 362578 | 12/2002 |
| JP | 2003-079388 | 3/2003 |
| JP | 2003-128835 | 5/2003 |
| JP | 2004 058010 | 2/2004 |
| JP | 2004-290130 | 10/2004 |
| JP | 2004 292705 | 10/2004 |
| JP | 2007 319092 | 12/2007 |
| JP | 2012 149273 | 8/2012 |
| JP | 2012-152171 | 8/2012 |
| JP | 2013 000099 | 1/2013 |
| JP | 5 630597 | 11/2014 |
| KR | 20110045975 | 5/2011 |
| WO | WO 89/10381 | 11/1989 |
| WO | WO 2005/026245 | 3/2005 |
| WO | WO 2010/012805 | 2/2010 |
| WO | WO 2010/081887 | 7/2010 |
| WO | WO 2011/039489 | 4/2011 |
| WO | WO 2013/144239 | 10/2013 |
| WO | WO 2014/079844 | 5/2014 |
| WO | WO 2014/122698 | 8/2014 |
| WO | WO 2014/167518 | 10/2014 |
| WO | WO 2014/167562 | 10/2014 |
| WO | WO 2015/067619 | 5/2015 |
| WO | WO 2015/097104 | 7/2015 |
| WO | WO 2015/173265 | 11/2015 |
| WO | WO 2016/198650 | 12/2016 |
| WO | WO 2016/198652 | 12/2016 |
| WO | WO 2017/108577 | 6/2017 |
| WO | WO 2017/198786 | 11/2017 |

OTHER PUBLICATIONS

Database WPI [Online] Accession No. 2012-Q50933, Sep. 9, 2012, p. 1, XP-002740253.
Database WPI [Online] Accession No. 2004-046313, May 8, 2003, pp. 1-2, XP-002740254.
Written Opinion in International Application No. PCT/EP2015/080557, dated Feb. 3, 2016, pp. 1-6.
Written Opinion in International Application No. PCT/EP2017/062028, dated Jun. 30, 2017, pp. 1-5.
Matsuda, E. et al. "Gene Cloning and Molecular Characterization of an Extracellular Poly($_L$-Lactic Acid) Depolymerase from *Amycolatopsis* sp. Strain K104-1" *Journal of Bacteriology*, Nov. 2005, pp. 7333-7340, vol. 187, No. 21.
Database WPI, Accession No. 2009-K99963, Jun. 17, 2009, pp. 1-2, XP-002690934.
Database WPI, Accession No. 2008-F66138, Dec. 13, 2007, pp. 1-2, XP-002690935.
Wang, Z.-Y. et al. "Gene Cloning and Characterization of a Poly($_L$-Lactic Acid) Depolymerase from *Pseudomonas* sp. Strain DS04-T" *J Polym Environ*, Aug. 28, 2011, pp. 827-833, vol. 19, No. 4.
Akutsu-Shigeno, Y. et al. "Cloning and Sequencing of a Poly($_{DL}$-Lactic Acid) Depolymerase Gene from *Paenibacillus amylolyticus* Strain TB-13 and Its Functional Expression in *Escherichia coli*" *Applied and Environmental Microbiology*, May 2003, pp. 2498-2504, vol. 69, No. 5.
Petrov, K. et al. "$_L$(+)-Lactic acid production from starch by a novel amylolytic *Lactococcus lactis* subsp. *lactis* 884" *Food Microbiology*, Jun. 2008, pp. 550-557, vol. 25.
Currently pending claims of U.S. Appl. No. 14/443,524, 2016, pp. 1-4.
Bernard, N. et al. "Cloning of the D-lactate dehydrogenase gene from *Lactobacillus delbrueckii* subsp. *bulgaricus* by complementation in *Escherichia coli*" *FEBS*, Sep. 1991, pp. 61-64, No. 1.
Wieczorek, A. et al. "Engineering the cell surface display of cohesins for assembly of cellulosome-inspired enzyme complexes on *Lactococcus lactis*" *Microbial Cell Factories*, Sep. 2010, pp. 1-13, Vo. 9, No. 69.
Wieczorek, A. et al. "Effects of synthetic cohesin-containing scaffold protein architecture on binding dockerin-enzyme fusions on the surface of *Lactococcus lactis*" *Microbial Cell Factories*, 2012, pp. 1-13, vol. 160, No. 11.
Koukiekolo, R. et al. "Degradation of Corn Fiber by *Clostridium cellulovorans* Cellulases and Hemicellulases and Contribution of Scaffolding Protein CbpA" *Applied and Environmental Microbiology*, Jul. 1, 2005, pp. 3504-3511, vol. 71, No. 7.
Cha, J. et al. "Effect of Multiple Copies of Cohesins on Cellulase and Hemicellulase Activities of *Clostridium cellulovorans* Minicellulosomes" *Journal of Microbiology and Biotechnology*, 2007, pp. 1782-1788, vol. 17, No. 11.
Kataeva, I. et al. "Interaction between *Clostridium thermocellum* endoglucanase CelD and polypeptides derived from the cellulosome-integrating protein CipA: stoichiometry and cellulolytic activity of the complexes" *Biochemical Journal*, 1997, pp. 617-624, vol. 326, No. 2.
Wen, F. et al. "Yeast Surface Display of Trifunctional Minicellulosomes for Simultaneous Saccharification and Fermentation of Cellulose to Ethanol" *Applied and Environmental Microbiology*, Feb. 1, 2010, pp. 1251-1260, vol. 76, No. 4.
Hyeon, J. E. et al. "Production of minicellulosomes for the enhanced hydrolysis of cellulosic substrates by recombinant *Corynebacterium glutamicum*" *Enzyme and Microbial Technology*, 2011, pp. 371-377, vol. 48.
Sun, J. et al. "Direct Conversion of Xylan to Ethanol by Recombinant *Saccharomyces cerevisiae* Strains Displaying an Engineered Minihemicellulosome" *Applied and Environmental Microbiology*, Jun. 2012, pp. 3837-3845, vol. 78, No. 11.
Database EMBL [Online] Accession No. HC441374, "Sequence 9 from Patent WO2010012805" Feb. 20, 2010, pp. 1-3, XP-002697306.
Database Geneseq [Online] Accession No. AZM34659, "*Clostridium* sp. Cellulose-binding protein-A (CbpA) DNA SEQ: 6" Oct. 13, 2011, p. 1, XP-002697307.
Written Opinion in International Application No. PCT/EP2013/061413, dated Aug. 5, 2013, pp. 1-7.
Devos, D. et al. "Practical Limits of Function Prediction" *Proteins: Structure, Function and Genetics*, 2000, pp. 98-107, vol. 41.
Whisstock, J. C. et al. "Prediction of protein function from protein sequence and structure" *Quarterly Reviews of Biophysics*, 2003, pp. 307-340, vol. 36, No. 3.
Witkowski, A. et al. "Conversion of a β-Ketoacyl Synthase to a Malonyl Decarboxylase by Replacement of the Active-Site Cysteine with Glutamine" *Biochemistry*, 1999, pp. 11643-11650, vol. 38.
Kisselev, L. "Polypeptide Release Factors in Prokaryotes and Eukaryotes: Same Function, Different Structure" *Structure*, Jan. 2002, pp. 8-9, vol. 10.
Database WPI, Accession No. 2005-262580, Mar. 24, 2005, pp. 1-3, XP-002690554.
Database WPI, Accession No. 2004-751104, Oct. 21, 2004, pp. 1-2, XP-002690555.
Currently pending claims of U.S. Appl. No. 14/387,285, 2014, pp. 1-3.
Yoshida, S. et al. "A bacterium that degrades and assimilates poly(ethylene terephthalate)" *Science*, Mar. 11, 2016, pp. 1196-1199, vol. 351.
Demirel, B. et al. "Crystallization Behavior of PET Materials" *BAU Fen Bil. Enst. Dergisi Cilt*, 2011, pp. 26-35, vol. 13, No. 1.
Kyrikou, I. et al. "Biodegradation of Agricultural Plastic Films: A Critical review" *J Polym Environ*, 2007, pp. 125-150, vol. 15.
Chen, S. et al. "Identification and Characterization of Bacterial Cutinase" *The Journal of Biological Chemistry*, Sep. 19, 2008, pp. 25854-25862, vol. 238, No. 38.
Ronkvist, A. M. et al. "Cutinase-Catalyzed Hydrolysis of Poly(ethylene terephthalate)" *Macromolecules*, 2009, pp. 5128-5138, vol. 42.

(56) References Cited

OTHER PUBLICATIONS

Nabil, H. et al. "Recycled Polyethylene Terephthalate Filled Natural Rubber Compounds: Effects of Filler Loading and Types of Matrix" *Journal of Elastomers and Plastics*, 2011, pp. 1-21, vol. 00-2011.

Bartolome, L. et al. "Recent Developments in the Chemical Recycling of PET" Material Recycling—Trends and Perspectives, Mar. 16, 2012, pp. 1-21.

Arutchelvi, J. et al. "Biodegradation of polyethylene and polypropylene" *Indian Journal of Biotechnology*, Jan. 2008, pp. 9-22, vol. 7.

Iwamoto, A. et al. "Enzymatic degradation of plastics containing polycaprolactone" *Polymer Degradation and Stability*, Jan. 1, 1994, pp. 205-213, vol. 45.

Mueller, R.-J. "Biological degradation of synthetic polyesters—Enzymes as potential catalysts for polyester recycling" *Process Biochemistry*, 2006, pp. 2124-2128, vol. 41, No. 10.

Written Opinion in International Application No. PCT/EP2014/073742, dated Aug. 8, 2015, pp. 1-5.

Herrero Acero, E. et al. "Enzymatic Surface Hydrolysis of PET: Effect of Structural Diversity on Kinetic Properties of Cutinases from *Thermobifida*" *Macromolecules*, 2011, pp. 4632-4640, vol. 44, No. 12.

Herrero Acero, E. et al. "Surface Engineering of a Cutinase From *Thermobifida cellulosilytica* for Improved Polyester Hydrolysis" *Biotechnology & Bioengineering*, Oct. 2013, pp. 2581-2590, vol. 110, No. 10.

Shah, A. A. et al. "Degradation of aliphatic and aliphatic-aromatic co-polyesters by depolymerases from *Roseateles depolymerans* strain TB-87 and analysis of degradation products by LC-MS" *Polymer Degradation and Stability*, Oct. 16, 2013, pp. 2722-2729, vol. 98, No. 12.

Written Opinion in International Application No. PCT/EP2015/060521, dated Jul. 20, 2015, pp. 1-6.

Wikipedia, https://web.archive.org/web/20130424032652/https://en.wikipedia.org/wiki/Polyethylene_terephthalate, archived Apr. 24, 2013, accessed Aug. 13, 2018, pp. 1-13.

Sukkhum, S. et al. "A novel poly ($_L$-lactide) degrading actinomycetes isolated from Thai forest soil, phylogenic relationship and the enzyme characterization" *The Journal of General and Applied Microbiology*, 2009, pp. 459-467, vol. 55, No. 6.

Sukkhum, S. et al. "Poly($_L$-Lactide)-Degrading Enzyme Production by *Actinomadura keratinilytica* T16-1 in 3 L Airlift Bioreactor and Its Degradation Ability for Biological Recycle" *Journal of Microbiology and Biotechnology*, Jan. 28, 2012, pp. 92-99, vol. 22, No. 1.

Written Opinion in International Application No. PCT/EP2015/074222, dated Feb. 1, 2016, pp. 1-5.

Niaounakis, 2013. Chapter 4: Disposal. Biopolymers Reuse, Recycling, and Disposal. A Volume in Plastics Design Library, a PDL Handbook Series. ISBN 978-1-4557-3145-9, published by Elsevier Inc, pp. 107-150.

Sugimori, Mar. 2013. Protease, washing agent containing the protease, and method of manufacturing the washing agent. EMBL AB809463, pp. 1-2.

Gouda, M. K. et al. "Production of a Polyester Degrading Extracellular Hydrolase from *Thermomonospora fusca*" *Biotechnology Progress*, Sep. 2002, pp. 927-934, vol. 18, No. 5.

Oda, Y. et al. "Degradation of Polylactide by Commercial Proteases" *Journal of Polymers and the Environment*, Jan. 2000, pp. 29-32, vol. 8, No. 1.

Written Opinion in International Application No. PCT/EP2016/055348, dated Jun. 2, 2016, pp. 1-6.

Database UniProt [Online] Accession No. I0LED3, Jun. 13, 2012, pp. 1-2, XP-002743807.

Database Geneseq [Online] Accession No. BAJ28992, Jan. 31, 2013, pp. 1-10, XP-002743803.

Database Geneseq [Online] Accession No. BAJ28991, Jan. 31, 2013, pp. 1-2, XP-002743804.

Database UniProt [Online] Accession No. F4F956, Jun. 28, 2011, pp. 1-2, XP-002743805.

Database UniProt [Online] Accession No. A8LWF7, Dec. 4, 2007, p. 1-2, XP-002743806.

Written Opinion in International Application No. PCT/EP2016/063369, dated Aug. 1, 2016, pp. 1-6.

Written Opinion in International Application No. PCT/EP2016/063373, dated Aug. 8, 2017, pp. 1-7.

Okino, S. et al. "Production of D-lactic acid by *Corynebacterium glutamicum* under oxygen deprivation" *Applied Microbiology and Biotechnology*, Jan. 10, 2008, pp. 449-454, vol. 78, No. 3.

Database WPI [Online] Accession No. 2012-K88398, Jan. 27, 2011, pp. 1-2, XP-002759107.

Written Opinion in International Application No. PCT/EP2016/081205, dated Jun. 1, 2017, pp. 1-19.

Currently pending claims of U.S. Appl. No. 16/302,107, 2018, pp. 1-4.

Currently pending claims of U.S. Appl. No. 16/064,494, 2018, pp. 1-3.

\* cited by examiner

PLASTIC COMPOUND AND PREPARATION PROCESS

CROSS-REFERENCE TO RELATED APPLICATION

This application is the U.S. national stage application of International Patent Application No. PCT/EP2015/080557, filed Dec. 18, 2015.

FIELD OF THE INVENTION

The present invention relates to novel plastic compounds, their preparation and use. The invention more particularly relates to polyolefin-containing plastic compounds having increased and controlled biodegradability. The plastic compounds of the invention contain in their structure, a biological entity that can degrade polyolefins, thereby improving biodegradation of the plastic under environmental conditions. The invention further relates to a process for producing such plastic compounds, as well as to plastic articles made from such plastic compounds.

BACKGROUND OF THE INVENTION

Plastics are inexpensive and durable materials, which are employed to manufacture a variety of products that find uses in a wide range of applications. As a consequence, the production of plastics has increased dramatically over the last decades. Among them, one of the largest groups is the group of polyolefin-based plastics. For instance, in Europe, polyolefins represent nearly half of the total volume of the plastics produced. Indeed, polyolefins may be used in a wide range of applications, including packaging (e.g.; trays, containers, bottles, bags, etc.), blown films (e.g.; bags and sacks), clothing field (e.g.; under garments for wetsuits), agricultural industry (e.g.; mulching films used to cover seeds or planted seedlings, silage films), etc. Polyolefin polymers that are most often used include polyethylene (PE) and/or polypropylene (PP), because of their low cost and mechanical properties adapted to almost all applications.

About 40% of polyolefin-based plastics are used for single-use disposable applications, or for short-lived products that are discarded within a year of manufacture. Because of the durability of the polymers involved, substantial quantities of plastics are piling up in landfill sites and in natural habitats worldwide, generating increasing environmental problems. As a consequence, more than 100 million tons of plastic wastes per year are produced, that predominantly contain polyolefins that end up as litter in the environment. Conventional polyolefins are considered as highly resistant to biodegradation, because of their high molecular mass values, hydrophobicity, crystallinity and lack of chemical functions such as alcohol, ester and acid, so that they may persist in the environment for decades, increasing environmental problems.

Different physical, chemical and/or biochemical approaches have been developed to reduce the biodegradation resistance of polyolefin-containing plastics. For instance, plastic articles made from a mix of polyolefins and biodegradable polymers, which may be natural (e.g., starch or cellulose) or synthetic, have been proposed. However, such kind of mixed plastic is both expensive, not easily processed, and exhibits weak mechanical properties. Moreover, only the biodegradable part of the corresponding mixed plastic article is degraded, the polyolefins remaining essentially non-degraded. An alternative to conventional, bio-inert polyolefin-containing plastics has also been developed using oxo-(bio)degradable polyolefins. However, the complete degradation of such plastics requires a two-stage process, involving oxidative degradation followed by the biodegradation of the oxidation product (for example alkanes, alcohols, aldehydes, esters, lactones, ketones and hydroperoxides). Up to now, there is no evidence that natural environmental conditions can allow biodegradation of oxo-degradable polyolefins up to carbon dioxide, water and biomass and it seems, to the contrary, that such oxo-degradable polyolefins are fragmented into smaller parts that still persist in the environment in a reasonable time allowing the non accumulation of degradation products.

There is thus a need for polyolefin-containing plastics having improved biodegradability that may be entirely degraded, under conditions generally encountered in the natural environment and/or in biodegradation process.

SUMMARY OF THE INVENTION

The present invention provides novel polyolefin-based plastic compounds having high biodegradation capacity. The plastic compounds of the invention contain biological entities that can degrade a polyolefin, which are embedded into the mass of the compounds. The inclusion of the biological entities into the structure of the plastic compounds substantially improves the degradability of said plastic, without impairing its mechanical properties. The presence of these biological entities makes it possible to control the conditions and the rate of degradation of the plastic compounds of the invention.

Thus, the invention relates to a plastic compound comprising at least one polyolefin and one biological entity that degrades said polyolefin.

Advantageously, the biological entity comprises an oxidase and/or a microorganism expressing and excreting an oxidase.

In a particular embodiment, the plastic compound further comprises a biological entity that degrades at least one oxidation product of the polyolefin, such as an alkane hydroxylase or an alcohol dehydrogenase or an aldehyde dehydrogenase, and/or a microorganism expressing an enzyme degrading polyolefin oxidation products such as an alkane hydroxylase and/or an alcohol dehydrogenase and/or an aldehyde dehydrogenase.

It is a further object of the invention to provide a process for preparing such a plastic compound, wherein at least one polyolefin and one biological entity that degrades said polyolefin are mixed at a temperature at which the polyolefin is in a partially or totally molten state. In a particular embodiment, the temperature is between the glass transition temperature and the melting point of said polyolefin. In another embodiment, the temperature is the melting point of said polyolefin, or above the melting point. In a particular embodiment, the temperature is between 80 and 250° C., preferably between 180 and 210° C.

It is a further object of the invention to provide a process for preparing a plastic article wherein at least one polyolefin and one biological entity that degrades said polyolefin are mixed at a temperature at which the polyolefin is in a partially or totally molten state.

It is also an object of the invention to provide a process for preparing a plastic compound or a plastic article comprising a polyolefin and one biological entity that degrades said polyolefin, comprising a step of extruding the polyolefin with the biological entity, performed at a temperature at which the polyolefin is in a partially or totally molten state. The invention also relates to a plastic article made with a plastic compound of the invention.

The invention further relates to a plastic article containing at least one polyolefin and one biological entity that is able to degrade said polyolefin in said plastic material, said biological entity comprising preferably an oxidase, preferably selected from the group consisting of laccase, peroxidase, oxygenase, lipoxygenase, monoxygenase, lignolytic enzyme, and/or a microorganism expressing and excreting an oxidase. The plastic article of the invention may further contain a biological entity that degrades at least one oxidation product of the polyolefin.

It is also an object of the invention to provide a method for increasing biodegradability of a polyolefin containing plastic article, comprising embedding in said plastic article an oxidase and optionally a microorganism or an enzyme degrading polyolefin oxidation products such as an alkane hydroxylase or an alcohol dehydrogenase or an aldehyde dehydrogenase.

DETAILED DESCRIPTION

Definition

The present disclosure will be best understood by reference to the following definitions.

In the context of the invention, the term "polyolefin" designates a class of homo- or copolymers containing an olefin, also called alkene, as a monomer. Polyolefins for use in the invention may be selected from polyethylene, polypropylene, polymethylpentene, polybutene-1, polyisobutylene, ethylene propylene rubber, ethylene propylene diene monomer rubber, ethylene vinyl alcohol, ethylene-carbon monoxide copolymer and copolymers and modifications thereof. According to the invention the term polyolefin also encompasses a functionalized polyolefin that has been modified to incorporate on its backbone, polar, oxygen-containing groups such as an acid, an alcohol, a ketone, an ester, an anhydride, a carboxylic acid, an epoxy group and/or double bonds and/or any reactive group. Such groups are dispersed along the polyolefin backbone, more preferably between every 20 to 1000 carbon atoms, more preferably between every 50 to 500 carbons atoms, and even more preferably between every 50 to 100 carbon atoms. According to the invention, the term polyolefin also encompasses a grafted polyolefin that has been modified by the addition of a functional monomer along its backbone, for example maleic anhydride, glycidyl methacrylate, acetic anhydride, stearic acid, maleic anhydride, glycidyl methacrylate, silane, isocyanate, and methyl methacrylate. Such a modified polyolefins, may be obtained via chemical, biological or physical treatments. According to the invention, the term polyolefin also encompasses a polyolefin mixed with pro-oxidants to form "oxo-degradable polyolefin". In the context of the invention, the terms "oxo-degradable polyolefin" or "oxo-biodegradable polyolefin" designate a polyolefin that contains pro-oxidant additives. The pro-oxidants may be organic or metallic such as metal carboxylates such as metal salts, especially Mn stearate and Fe stearate. These pro-oxidants are advantageously used to accelerate the degradation in the presence of oxygen, UV and/or heat.

In the context of the invention, a "plastic compound" refers to a plastic formulation, in a molten or solid state, that is suitable for making a plastic article. A plastic compound of the invention is typically a homogeneous blend of at least one polyolefin and a biological entity that degrades it. Preferably, the plastic compound is constituted of a mix of semi-crystalline and/or amorphous polymers, or semi-crystalline polymers and additives.

The term "polyethylene", in the context of the invention, refers to a polymer consisting of repeating units of ethylene. Polyethylene can be found under different forms which are varying according to its type of branching, its crystal structure and its molecular weight (between 5000 g/mol and 300000 g/mol, preferably between 10000 g/mol and 200 000 g/mol, more preferably between 20000 g/mol and 150000 g/mol). The term "polyethylene" includes Ultra-high-molecular-weight polyethylene (UHMWPE), Ultra-low-molecular-weight polyethylene (ULMWPE or PE-WAX), High-molecular-weight polyethylene (HMWPE), High-density polyethylene (HDPE), High-density cross-linked polyethylene (HDXLPE), Cross-linked polyethylene (PEX or XLPE), Medium-density polyethylene (MDPE), Linear low-density polyethylene (LLDPE), Low-density polyethylene (LDPE), Very-low-density polyethylene (VLDPE), and/or Chlorinated polyethylene (CPE).

Within the context of the invention, the term "plastic article" refers to any item made from at least one plastic material, such as plastic sheet, tube, rod, profile, shape, massive block, fiber, etc. Plastic articles may contain additional substances or additives, such as plasticizers, mineral or organic fillers. Preferably the plastic product is constituted of a mix of semi-crystalline and/or amorphous polymers, or semi-crystalline polymers and additives. Preferably, the plastic article is a manufactured product, such as a rigid or flexible packaging, agricultural films, bags and sacks, disposable items or the like.

Plastic Compound

The present invention provides new plastic compounds that can be used for making biodegradable polyolefin-containing plastic articles.

According to the invention, the plastic compound comprises at least one polyolefin and a biological entity that can degrade said polyolefin.

Advantageously, the polyolefin is selected from the group consisting of polyethylene, polypropylene, polymethylpentene, polybutene-1, polyisobutylene, ethylene propylene rubber, ethylene propylene diene monomer rubber, ethylene vinyl alcohol, ethylene-carbon monoxide copolymer and copolymers thereof.

In a particular embodiment, the plastic compound comprises at least one polyethylene, preferably selected from Low-density polyethylene (LDPE), High-density polyethylene (HDPE) or Linear low-density polyethylene (LLDPE).

According to the invention, the plastic compound may comprise two or more polyolefins.

Alternatively or in addition, the plastic compound may comprise additional polymer(s), such as polyesters, polyamides or vinyl polymers, lignin, cellulose or hemi-cellulose, starch and derivatives thereof.

In a particular embodiment, the plastic compound comprises one or more polyolefins and one or more polyesters. Preferred polyesters are chosen among polyethylene terephthalate (PET), polytrimethylene terephthalate (PTT), polybutylene terephthalate (PBT), polyethylene isosorbide terephthalate (PEIT), polylactic acid (PLA), poly(L-lactic acid) (PLLA), poly(D-lactic acid) (PDLA), poly(D,L-lactic acid) (PDLLA), PLA stereocomplex (scPLA), polyglycolic acid (PGA), polyhydroxyalkanoate (PHA), poly(3-hydroxybutyrate) (P(3HB)/PHB), poly(3-hydroxyvalerate) (P(3HV)/PHV), poly(3-hydroxyhexanoate) (P(3HHx)), poly (3-hydroxyoctanoate) (P(3HO)), poly(3-hydroxydecanoate) (P(3HD)), Poly(3-hydroxybutyrate-co-3-hydroxyvalerate) (P(3HB-co-3HV)/PHBV), poly(3-hydroxybutyrate-co-3- hydroxyhexanoate) (P(3HB-co-3HHx)/(PHBHHx)), poly(3-hydroxybutyrate-co-5-hydroxyvalerate) (PHB5HV), poly (3-hydroxybutyrate-co-3-hydroxypropionate) (PHB3HP), polyhydroxybutyrate-co-hydroxyoctonoate (PHBO), polyhydroxybutyrate-co-hydroxyoctadecanoate (PHBOd), poly (3-hydroxybutyrate-co-3-hydroxyvalerate-co-4-hydroxybutyrate) (P(3HB-co-3HV-co-4HB)), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA), polyethylene naphthalate (PEN), polycyclohexylenedimethylene terephthalate (PCT) and blends/mixtures of these materials.

According to the invention, the biological entity preferably comprises an enzyme, more preferably an oxidase. The term "oxidase", in the context of the invention, refers to an enzyme that induces, facilitates or accelerates oxidation of a polyolefin. A preferred non-limiting list of oxidases includes laccase, peroxidase, oxygenase, lipoxygenase, mono-oxygenase, lignolytic enzyme.

In a particular embodiment, the plastic compound comprises a laccase. The laccase is advantageously able to oxidize a mediator, which in turn will oxidize the polyolefin. Such mediator may be commonly present in the environment or may be provided during the degradation process, such as during an abiotic degradation of the polyolefin. Alternatively, the plastic compound may comprise such a mediator or a product that generates mediator. For instance, the plastic compound comprises an anti-oxidant, a lignocellulosic compound or an aromatic molecule as a mediator. In another embodiment, the plastic compound comprises a peroxidase, such as a manganese peroxidase. In a further embodiment, the plastic compound comprises a lipoxygenase. Advantageously, such plastic compound may further comprise a fatty acid as a substrate for the lipoxygenase. In another embodiment, the plastic compound contains a mono-oxygenase. The plastic compound of the invention may comprise at least two or more oxidases. The plastic compound of the invention may also comprise an inductor of oxidase production by the microorganism such as cellulose, lignin, ligno-cellulose or its derivative or metal.

More precisely, oxidases can be selected from:
Laccase from *Trametes versicolor* (Fujisawa et al., 2001)
Laccase from *Rhodococcus ruber* DSM 45332 or from *Rhodococcus rhodochrous* ATCC29672
Lignine peroxydase from *Streptomyces viridosporus* T7A, *S. badius* 252 or *S. setonii* (Pometto et al., 1992)
Lignolytic enzymes *Pleurotus ostreatus*, from *Streptomyces viridosporus*, or *S. badius*, or *S. setonii*, or *Phanerochaete chrysosporium*, or *Fusarium moniliforme*, or *F. nivale*, or *F. oxysporum*, or *F. roseium*, or *F. tricinctum*, or *Coriolus versicolor* (Pometto, 1992)
Mn peroxidase from *Phanerochaete chrysosporium* (Tetsuya, 1996)

The enzyme may be natural or synthetic. For example, the enzyme may be produced by recombinant techniques, or it may be isolated or purified from natural sources, when naturally-occurring, or it may be artificially produced.

In a particular embodiment, the enzyme(s) is(are) in an isolated or purified form. Preferentially, the enzymes for use in the invention are expressed, derived, secreted, isolated, or purified from microorganisms, including recombinant microorganisms. The enzymes may be purified by techniques known per se in the art, and stored under conventional techniques. The enzymes may be further modified to improve e.g., their stability or activity.

In a particular embodiment, the biological entity comprises a microorganism expressing and excreting the enzyme e.g., the oxidase. The microorganism can be selected from the group consisting of bacteria, yeasts and fungi. In the context of the invention, the term "microorganism" also includes spores. The microorganism may naturally synthesize the oxidase, or it may be a recombinant microorganism.

Examples of microorganisms expressing and excreting an oxidase include *Acidianus* sp., *Acidithiobacillus* sp., *Acidiphilium* sp., *Acinetobacter* sp., *Actinopolyspora* sp., *Alcaligenes* sp., *Aeromonas* sp., *Alcanivorax* sp., *Aliivibrio* sp., *Alteromonas* sp., *Aminobacter* sp., *Amycolicicoccus* sp., *Aquabacterium* sp., *Archaeoglobus* sp., *Arhodomonas* sp., *Arthrobacter* sp., *Aspergillus* sp., *Bacillus* sp., *Bacterium* sp., *Brachybacterium* sp., *Beauveria* sp., *Brevibacillus* sp., *Brevundimonas* sp., *Brucella* sp., *Burkholderia* sp., *Candida* sp., *Carica* sp., *Cellulomonas* sp., *Chromohalobacter* sp., *Clostridium* sp., *Colletotrichum* sp., *Colwellia* sp., *Comamonas* sp., *Coriolus* sp., *Corynebacteriaceae*, *Curtobacterium* sp., *Curvularia* sp., *Desulfatibacillum* sp., *Desulfosarcina* sp., *Desulfococcus* sp., *Desulfomicrobium* sp., *Desulfotalea* sp., *Desulfocapsa* sp., *Desulfuromonas* sp., *Desulfocapsa* sp., *Dictyoglomus* sp., *Dietzia* sp., *Drechslera* sp., *Enterobacter* sp., *Escherichia* sp., *Flavimonas* sp., *Flavobacterium* sp., *Fusarium* sp., *Geobacillus* sp., *Geobacter* sp., *Glaciecola* sp., *Gordonia* sp., *Haloarcula* sp., *Halobacterium* sp., *Haloferax* sp., *Halomonas* sp., *Halorubrum* sp., *Hansenula* sp., *Ketogulonicigenium* sp., *Kluyveromyces* sp., *Kocuria* sp., *Lasiodiplodia* sp., *Leptothrix* sp., *Lysinibacillus* sp., *Marinobacter* sp., *Methanococcoides* sp., *Methanosarcina* sp., *Microbacteriaceae*, *Microbacterium* sp., *Micrococcus* sp., *Mucor* sp., *Mycobacterium* sp., *Nocardia* sp., *Ochrobactrum* sp., *Oceanobacter* sp., *Octadecabacter* sp., *Paecilomyces* sp., *Paenibacillus* sp., *Papulaspora* sp., *Paracoccus* sp., *Parvibaculum* sp., *Penicillium* sp., *Phanerochaete* sp., *Photobacter* sp., *Photorhabdus* sp., *Planococcus* sp., *Plodia* sp., *Pleurotus* sp., *Propagules* sp., *Proteobacterium* sp., *Pseudomonas* sp., *Pseudoalteromonas* sp., *Pseudonocardiaceae*, *Psychrobacter* sp., *Psychroflexus* sp., *Psychromonas* sp., *Ralstonia* sp., *Rhizopus* sp., *Rhodobacter* sp., *Rhodococcus* sp., *Salinisphaera* sp., *Shewanella* sp., *Sphingomonas* sp., *Saccharomyces* sp., *Stenotrophomonas* sp., *Streptomyces* sp., *Sulfolobus* sp., *Terroglobus* sp., *Thalassolituus* sp., *Thelassobacillus* sp., *Thermooleophilum* sp., *Thermus* sp., *Thiobacillus* sp., *Thioclava* sp., *Trametes* sp., *Trichoderma* sp. *Tsukamurella* sp., *Vibrio* sp., *Vogesella* sp., *Weeksella* sp., *Xylella* sp. and consortium or mixtures of said microorganisms.

Advantageously, the biological entity/polyolefin ratio in the plastic compound is comprised between 0.1 and 10, preferentially between 0.5 and 8, preferentially between 1 and 6, preferentially between 1 and 5, preferentially between 1 and 4, preferentially between 1 and 3, preferentially between 1.5 and 3, and even more preferentially this ratio is about 2. This ratio may be easily adapted by a person skilled in the art depending on the polyolefin, the nature of the biological entity used, and the desired results, especially in terms of degradability of the plastic compound.

In a further embodiment, the plastic compound of the invention comprises a biological entity that degrades at least one oxidation product of the polyolefin, such as alkanes. Advantageously, the biological entity that degrades oxidation products of polyolefin comprises an alkane hydroxylase or an alcohol dehydrogenase or an aldehyde dehydrogenase or a microorganism expressing an alkane hydroxylase and/or an alcohol dehydrogenase and/or an aldehyde dehydrogenase.

A preferred non-limiting list of enzymes able to degrade oxidation include products include hydrolase, oxidoreductase, oxygenase, dioxygenase, mono-oxygenase, alkane mono-oxygenase, alcohol dehydrogenase, Baeyer Villiger mono-oxygenase, aldehyde dehydrogenase, fatty acid mono-oxygenase, dioxygenase, methane mono-oxygenase, propane mono-oxygenase, butane mono-oxygenase, luciferase, esterase. A particular example of alkane hydroxylase include enzymes encoded by LadA and AlmA genes (LadA is a thermophilic soluble LC-alkane mono-oxygenase from *Geobacillus* and AlmA is a LC-alkane mono-oxygenase from *Acinetobacter*; see Wang et al; 2013).

In a particular embodiment, the plastic compound comprises a microorganism expressing and excreting both an oxidase and an enzyme degrading oxidation products of the polyolefin such as an alkane hydroxylase or an alcohol dehydrogenase or an aldehyde dehydrogenase.

In order to optimize the biodegradability, the plastic compound may further comprise at least one pro-oxidant element. The term "pro-oxidant" or "pro-degradant" refers, in the context of the invention, to additives that accelerate the degradation of a polymer by fostering its oxidation and its fragmentation when exposed to heat, air and/or light. According to the invention, pro-oxidants degrade the polymers into fragments with reduced molecular weights. For instance, the use of pro-oxidants allows to reduce the molecular weight of the polyolefins from 150 000 g/mol or higher to about 5 000 to 10000 g/mol in a reasonable time (less than 2 years). Pro-oxidants are most often transition metals, typically metal salts of carboxylic acids that drive the oxidation process which, under the action of heat or light, will reduce the molecular weight of the polymer.

In a particular embodiment, the pro-oxidant is a metallic agent such as a metal carboxylate. For instance, the plastic compound of the invention comprises cobalt stearate, iron stearate, manganese stearate, zinc stearate and/or nickel stearate, more preferably a mix of manganese stearate and iron stearate.

The plastic compound of the invention may further comprise one or more additives, preferably selected from the group consisting of plasticizers, coloring agents, processing aids, rheological agents, anti-static agents, anti-UV agents, toughening agents, anti-fogging agents, compatibilizers, slip agents, flame retardant agents, anti-oxidants and light stabilizers.

Process for Preparing the Plastic Compound and/or Plastic Article

The invention further relates to a process for producing a biodegradable polyolefin-containing plastic compounds as defined above. The invention further relates to a process for producing directly a polyolefin containing plastic article. The present invention indeed shows that biological entities as defined above may be included in polyolefins under conditions allowing to retain a biological or enzymatic activity in the resulting plastic compound or article. More particularly, the invention shows that such plastic compounds may be produced by mixing the ingredients under heating to ensure a homogeneous blend.

More particularly, the invention thus relates to a process for preparing such a plastic compound, wherein the polyolefin and the biological entities are mixed at a temperature at which the polyolefin is in a partially or totally molten state. The resulting compound includes the biological entity that substantially improves the degradability of the polyolefin, without impairing the mechanical properties of the polymer. Thus, the plastic compound obtained according to the process of the invention is highly suitable for the standard operations of plastics processing.

The invention further relates to a process for preparing a plastic article wherein at least one polyolefin and one biological entity that degrades said polyolefin are mixed at a temperature at which the polyolefin is in a partially or totally molten state.

Advantageously, the biological entity and the polyolefin are mixed at a temperature between the glass transition temperature and the melting point of the polyolefin. Alternatively, the biological entity and the polyolefin are mixed at the melting point of said polyolefin, or above. In a particular embodiment, they are mixed at a temperature between 80° C. and 250° C., preferably between 180° C. and 210° C.

According to the invention, the compounding or plastic article manufacturing may be performed using extrusion, twin screw extrusion, single screw extrusion, injection-molding, casting, thermoforming, rotary molding, compression, calendering, ironing, coating, stratification, expansion, pultrusion, extrusion blow-molding, extrusion-swelling, compression-granulation or water-in-oil-in-water double emulsion evaporation. The resulting plastic compound or plastic article integrates the biological entity (enzymes and/or microorganisms) that is embedded in the mass of the compound.

In a preferred embodiment, the process for preparing a plastic compound or plastic article comprises a step of extruding the polyolefin with the biological entity, performed at a temperature at which the polyolefin is in a partially or totally molten state.

The term "extrusion" means the preparation of a polymer in a desired form, using an extruder. This term encompasses profiled extrusion, extrusion blow-molding, extrusion-swelling and extrusion-calendering. The extrusion step takes place at a temperature in which the polymer is in a partially or totally molten state. The temperature may vary depending both of the polyolefin and of the nature of the biological entity. This temperature may be readily determined by a person skilled in the art, in the light of his general knowledge. Under the action of the temperature and pressure, the polyolefin in molten or partially molten form mixes with the other starting materials, and especially the biological entity.

In a preferred embodiment, the biological entity comprises an oxidase, such as laccase, peroxidase, oxygenase, lipoxygenase, mono-oxygenase, lignolytic enzyme, and/or a microorganism expressing and excreting the oxidase. In a particular embodiment, a biological entity that degrades at least one oxidation product of the polyolefin may also be admixed during the step of extruding. Said biological entity preferably comprises an enzyme degrading at least one oxidation product of the polyolefin such as an alkane hydroxylase or an alcohol dehydrogenase or an aldehyde dehydrogenase and/or a microorganism expressing an enzyme degrading at least one oxidation product of the polyolefin such as an alkane hydroxylase and/or an alcohol dehydrogenase and/or an aldehyde dehydrogenase.

The biological entity may be prepared before the process. For example, enzymes may be coated, or chosen from enzymes encapsulated in capsules consisting of the same material as said polymer, enzymes encapsulated in cage molecules and enzymes aggregated together. The enzymes may be obtained by encapsulation in capsules, preferentially in capsules consisting of polyolefins. The encapsulation techniques are well known to those skilled in the art. Typically, this encapsulation is performed by using emulsions.

If required, additional components, and more particularly additives, may be added during the extruding step, so that they are incorporated into the plastic compound mass.

Plastic Articles

The plastic compound of the invention makes it possible to produce biodegradable polyolefin containing plastic articles.

Within the context of the invention, the term "biodegradable polyolefin containing plastic article" refers to a polyolefin containing plastic article that can biodegrade totally in natural environmental conditions or in controlled environmental conditions such as industrial composting units in aerobic or anaerobic conditions.

According to the invention, plastic articles made with a plastic compound of the invention may be degraded up to molecules that may be consumed by microorganisms and return to compounds found in nature, such as carbon dioxide, water, biomass and/or methane. The invention makes it possible to degrade the polyolefins contained in the plastic compound and/or corresponding plastic articles to reduce their molecular weight from more to 150 000 to about 5000 or less, and then to molecules with molecular weight less than 1000, and preferably 500 or less, that may finally be consumed by microorganisms.

Accordingly, the invention provides a plastic article containing at least one polyolefin and one biological entity that is able to degrade said polyolefin in said plastic material. Advantageously, the biological entity comprises an oxidase, preferably selected from the group consisting of laccase, peroxidase, oxygenase, lipoxygenase, mono-oxygenase, lignolytic enzyme and/or a microorganism expressing and excreting an oxidase. In order to improve the degradability, the article may further contain a biological entity that degrades at least one oxidation product of the polyolefin. In a particular embodiment, the biological entity comprises a microorganism expressing and excreting both an oxidase and an enzyme degrading polyolefin oxidation products such as an alkane hydroxylase and/or an alcohol dehydrogenase and/or an aldehyde dehydrogenase.

Preferably, the biological entity/polyolefin ratio in the plastic article is between 0.1 and 10, preferentially between 1 and 4, and more preferentially is about 2.

It is also an object of the invention to provide a method for increasing biodegradability of a polyolefin containing plastic article, comprising embedding in said plastic article an oxidase and optionally a microorganism or an enzyme degrading polyolefin oxidation products such as an alkane hydroxylase or an alcohol dehydrogenase or an aldehyde dehydrogenase.

In a preferred embodiment, such method can be supplemented by an external treatment process such as an oxidation pretreatment process, for example using chemical, biological or physical processes, such as UV, light, oxygen, or heat.

Example 1: Preparation of a Polyethylene/Oxidase Compound According to the Invention The strain *Pleurotus ostreatus* DSM 1020 is cultivated in a minimal medium containing 1% cellulose to induce laccase production during 5 days at 28° C. The culture is centrifuged to eliminate biomass and residual cellulose. The crude supernatant is atomized to recover oxidase in the powder form.

The incorporation of oxidase into PE is performed during an extrusion step. An extruder of BC21 twin-screw type of Clextral brand (motor power 9 kW, maximum screw speed 600 rpm, maximum current 18.9 A) is used at 180° C. The screws have a diameter d of 25 mm and the separation between the two screws is 21 mm. The length of the sheath is 600 mm, i.e. a ratio L/d of 24.

The extrusion takes place in 5 steps:
1. introduction of a mixture of PE and laccases in feed hopper,
2. passage of said mixture into the extruder,
3. output of a rod through a circular die 3 mm in diameter,
4. cooling of the rod in a bath of cold water three meters long, followed by "drying" with pulsed cold air,
5. cutting in the form of regular granules by a system with a rotating knife.

The formulation may vary as a function of the polyolefin/oxidase ratio. In the present experiment, the resulting compound contains 2% (m/m) of oxidase powder in the material.

The granules obtained by extrusion are then dried in a rotary oven at 60° C. for 4 hours in a desiccant station so as to remove the residual water present, due to the passage into the tank of water.

Example 2: Biodegradation of a Polyethylene/Oxidase Compound

The compound obtained in Example 1 is placed in suspension in a minimal medium for 30 days at 28° C. At the end of the incubation, the residual compound is recovered, dried at 60° C. during 7 days and weighed.

The oxidase activity on PE is confirmed by a weight loss of 5%.

Example 3: Preparation of a Polyethylene/Oxidase/Pro-Oxydant Compound According to the Invention A plastic compound containing LLDPE, 2% of pro-oxidants Fe—Mn and 2% of microorganisms secreting a laccase (*Rhodococcus ruber* DSM 45332 and/or *R. rhodochrous* ATCC 29672) is prepared according to example 1.

A LLDPE film with a thickness of 10 µm is realized with said plastic compound and further artificially aged in order to reproduce a natural aging of one year: It is submitted to heat and UV in an incubator ATLAS SEPAP 12-24 at 60° C. during 80 h (corresponding to one summer season under temperate climate) and in an aerated incubator at 60° C. during 15 days (corresponding to behavior in soil following the Arrhenius law). This oxidized film is characterized by SEC in TCB and by IRTF-ATR.

60 mg of the LLDPE film are then placed in 10 mL of culture medium (S M Sivan et al., 2006) during 30 days at 28° C. At the end of incubation, the LLDPE film is recovered and analyzed in SEC and IRTF-ATR.

The LLDPE film is significantly further oxidized by the action of the laccase produced by the *Rhodococcus* contained in the film, as shown by SEC and IRTF-ATR results: the carbonyl index is increased and the molecular weight is decreased from around 7500 g/mol to a molecular weight of 500 g/mol.

Example 4: Bioassimilation of Oxidation Products

The residues from the LLDPE film treated in Example 3 are recovered and further incubated with *Rhodococcus opacus* DSM 43205. The strain growth is followed by turbidimetry.

Results show the same kinetics of growth for residues of LLDPE film and 0.1% mannitol, confirming the strain is able to assimilate the oxidation products.

The invention claimed is:

1. A plastic compound comprising at least one polyolefin, an oxidase that degrades said polyolefin and a biological entity, said biological entity comprising an alcohol dehydrogenase, an aldehyde dehydrogenase or a microorganism that expresses an alcohol dehydrogenase or an aldehyde dehydrogenase, wherein the biological entity degrades at least one oxidation product of the polyolefin and wherein the oxidase and the biological entity are embedded in the mass of the plastic compound.

2. The plastic compound of claim 1, wherein the biological entity that degrades at least one oxidation product comprises the microorganism that expresses an alcohol dehydrogenase or an aldehyde dehydrogenase.

3. The plastic compound of claim 1, further comprising at least one pro-oxidant element.

4. The plastic compound of claim 1, wherein the polyolefin is selected from the group consisting of polyethylene, polypropylene, polymethylpentene, polybutene-1, polyisobutylene, ethylene propylene rubber, ethylene propylene diene monomer rubber, ethylene vinyl alcohol, ethylene-carbon monoxide copolymer and copolymers thereof.

5. The plastic compound of claim 1, wherein the biological entity/polyolefin ratio is between 0.1 and 10.

6. The plastic compound of claim 5, wherein the biological entity/polyolefin ratio is between 1.5 and 3.

7. The plastic compound of claim 1, further comprising at least one additive.

8. The plastic compound of claim 1, further comprising at least one additional polymer selected from polyesters, polyamides, vinyl polymers, lignin, cellulose, hemi-cellulose, starch and derivatives thereof.

9. A process for preparing a plastic compound according to claim 1 wherein at least one polyolefin, an oxidase that degrades said polyolefin and a biological entity are mixed at a temperature at which the polyolefin is in a partially or totally molten state, wherein the biological entity degrades at least one oxidation product of the polyolefin and the biological entity comprises an alcohol dehydrogenase, an aldehyde dehydrogenase or a microorganism that expresses an alcohol dehydrogenase or an aldehyde dehydrogenase.

10. The process of claim 9, wherein the oxidase, the biological entity and the polyolefin are mixed at, or above, the melting point of said polyolefin.

11. A process for preparing a plastic article wherein at least one polyolefin, an oxidase that degrades said polyolefin and a biological entity that degrades at least one oxidation product of the polyolefin comprising are mixed at a temperature at which the polyolefin is in a partially or totally molten state, said biological entity comprising an alcohol dehydrogenase, an aldehyde dehydrogenase or a microorganism that expresses an alcohol dehydrogenase or an aldehyde dehydrogenase.

12. The process of claim 11, wherein the oxidase, the biological entity and the polyolefin are mixed at, or above, the melting point of said polyolefin.

13. A plastic article containing at least one polyolefin and an oxidase that is able to degrade said polyolefin in said plastic article, and a biological entity that degrades at least one oxidation product of the polyolefin, the biological entity selected from an alcohol dehydrogenase, an aldehyde dehydrogenase and a microorganism that expresses an alcohol dehydrogenase or an aldehyde dehydrogenase.

14. The plastic article of claim 13, wherein the oxidase/polyolefin ratio is between 0.1 and 10.

15. The plastic compound of claim 1, wherein the plastic compound is produced by mixing the polyolefin, the oxidase and the biological entity at a temperature at which the polyolefin is in a partially or totally molten state.

16. The plastic compound of claim 1, said plastic compound comprising a homogeneous blend of said at least one polyolefin, an oxidase that degrades said polyolefin and a biological entity that degrades at least one oxidation product of the polyolefin, said biological entity comprising an alcohol dehydrogenase, an aldehyde dehydrogenase or a microorganism that expresses an alcohol dehydrogenase or an aldehyde dehydrogenase.

17. The plastic article of claim 13, said plastic article comprising a homogeneous blend of said at least one polyolefin and an oxidase that is able to degrade said polyolefin.

18. The plastic compound of claim 1, comprising at least one polyolefin,
an oxidase that degrades said polyolefin wherein said enzyme is embedded in the mass of the plastic compound,
a biological entity selected from an alcohol dehydrogenase, an aldehyde dehydrogenase or a microorganism that expresses and excretes an alcohol dehydrogenase, an aldehyde dehydrogenase, said biological entity degrading at least one oxidation product of the polyolefin wherein said biological entity is embedded in the mass of the compound, and
at least one pro-oxidant element.

19. The plastic compound of claim 1, wherein the oxidase is selected from the group consisting of a laccase, a peroxidase, an oxygenase, a lipoxygenase, a mono-oxygenase, and a lignolytic enzyme.

* * * * *

UNITED STATES PATENT AND TRADEMARK OFFICE
CERTIFICATE OF CORRECTION

PATENT NO. : 10,626,242 B2
APPLICATION NO. : 15/536765
DATED : April 21, 2020
INVENTOR(S) : Thierry Ferreira, Frédérique Guillamot and Steven Colas It is certified that error appears in the above-identified patent and that said Letters Patent is hereby corrected as shown below:

In the Specification

<u>Column 7,</u>
Line 2, "oxidation include products include hydrolase," should read --oxidation products include hydrolase,--.

Signed and Sealed this
Fourth Day of August, 2020

Andrei Iancu
*Director of the United States Patent and Trademark Office*